US008373000B2

(12) United States Patent
Molock et al.

(10) Patent No.: US 8,373,000 B2
(45) Date of Patent: *Feb. 12, 2013

(54) PROCESS FOR THE PRODUCTION OF BIS(TRIMETHYLSILYLOXY)SILYLALKYL-GLYCEROL METHACRYLATES

(75) Inventors: Frank Molock, Orange Park, FL (US); Jason Garner, Jacksonville, FL (US); Shivkumar Mahadevan, Orange Park, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 2100 days.

This patent is subject to a terminal disclaimer.

(21) Appl. No.: 10/862,074

(22) Filed: Jun. 4, 2004

(65) Prior Publication Data

US 2008/0139829 A1  Jun. 12, 2008

Related U.S. Application Data

(60) Provisional application No. 60/483,846, filed on Jun. 30, 2003, provisional application No. 60/516,471, filed on Oct. 31, 2003.

(51) Int. Cl.
*C07F 7/04* (2006.01)
*C07F 7/08* (2006.01)
(52) U.S. Cl. ...................................... 556/437
(58) Field of Classification Search ................... 556/437
See application file for complete search history.

(56) References Cited

U.S. PATENT DOCUMENTS

| 3,746,734 A | 7/1973 | Berger |
| 3,875,211 A * | 4/1975 | Steckler ................ 560/209 |
| 3,878,263 A | 4/1975 | Martin |
| 4,139,513 A | 2/1979 | Tanaka et al. |
| 4,139,548 A | 2/1979 | Tanaka et al. |
| 4,139,692 A | 2/1979 | Tanaka et al. |
| 4,235,985 A | 11/1980 | Tanaka et al. |
| 5,032,628 A * | 7/1991 | Choi et al. ................ 523/409 |
| 5,072,027 A * | 12/1991 | Kobayashi et al. ........ 560/217 |
| 5,380,884 A * | 1/1995 | Hosokawa et al. ........ 549/515 |
| 5,907,025 A | 5/1999 | Brunelle |
| 6,126,855 A * | 10/2000 | Elliott ................ 252/299.01 |
| 6,891,055 B2 * | 5/2005 | Zanini et al. ............. 556/436 |
| 2002/0077491 A1 | 6/2002 | Shipps et al. |
| 2006/0012750 A1 | 1/2006 | Nakamura |

FOREIGN PATENT DOCUMENTS

| JP | 54055455 A | 5/1979 |
| JP | 54061126 A | 5/1979 |
| JP | 2002080538 A | 3/2002 |

OTHER PUBLICATIONS

A remarkable epoxide opening, An expeditious synthesis of vernolepin and vernomenin. Danishefsky, Samuel; Kitahara, Takeshi; Schuda, Paul F.; Etheredge, Sarah J. Dep. Chem., Univ. Pittsburgh, Pittsburgh, PA, USA. Journal of the American Chemical Society (1976), 98(10).
Corticosteroid analogs. XXI. Stereochemistry of opening of stereoisomeric oxides of 1-acetyl-4-tert-butyl-1-cyclohexene in the presence of ethyl hydrazinecarboxylate. Dobrynin, V. N.; Akhrem, A. A. N. D. Zelinskii Inst. Org. Chem., Moscow, USSR. Izvestiya Akademii Nauk SSSR, Seriya Khimicheskaya (1966), (11), 1969-74.
Lewis base-catalyzed addition of trialkylaluminum compounds to epoxides. Schneider, Christoph; Brauner, Jorg. Institut fur Organische Chemie, Gottingen, Germany. Eur. J. Org. Chem. (2001), (23), 4445-4450.
Total synthesis of capsanthin using Lewis acid-promoted regio- and stereoselective rearrangement of tetrasubstituted epoxide. Yamano, Yumiko; Ito, Masayoshi. Kobe Pharmaceutical University, Kobe, Japan. Chem. Pharm. Bull. (2001), 49(12), 1662-1663.
Stereochemistry control in the lewis acid mediated lactonization reaction of g,d-epoxy-b-silyloxy esters. Nacro, Kassoum; Gorrichon, Liliane; Escudier, Jean-Marc; Baltas, Michel. Lombardi Cancer Center, Georgetown University Medical Center, Washington, DC, USA. Eur. J. Org. Chem. (2001), (22), 4247-4258.
σ-π Chelation-controlled chemoselective ring openings of epoxides. Asao, N.; Kasahara, T.; Yamamoto, Y. Graduate School of Science, Department of Chemistry, Tohoku University, Sendai, Japan. Tetrahedron Lett. (2001), 42(44), 7903-7905.
Applications of Lewis acids for the efficient syntheses of diltiazem, cephems and taxoids. Hashiyama, Tomiki. Medicinal Chemistry Department, Discovery Research Laboratory, Tanabe Seiyaku Co Ltd, Toda, Saitama 335-8505, Jordan. Abstr. Pap.—Am. Chem. Soc. (2001), 221st ORGN-468.
Regio- and stereoselective synthesis of nor-nonactinic acid derivatives. Kinetic reaction control in the Lewis acid mediated domino reaction of 1,3-dicarbonyl dianions with 1-bromo-2,3-epoxypropanes. Langer, Peter; Freifeld, Ilia. Institut fur Organische Chemie der Georg-August-Universitat Gottingen, Gottingen, Germany. Chem.—Eur. J. (2001), 7(3), 565-572.
AlCl3 as an efficient Lewis acid catalyst in water. Fringuelli, F.; Pizzo, F.; Vaccaro, L. Dipartimento di Chimica, Universita Perugia, Perugia, Italy. Tetrahedron Lett. (2001), 42(6), 1131-1133.
Benzyloxymethyl group as a convertible internal ligand for La(OTf)3-catalyzed 7-endo ring-opening of hydroxy epoxide. Fujiwara, Kenshu; Morishita, Hiroshi; Tokiwano, Tetsuo; Mural, Akio. Division of Chemistry, Graduate School of Science, Hokkaido University, Sapporo, Japan. Heterocycles (2001), 54(1), 109-110.
Assessment of the negative factors responsible for the decrease in the enantioselectivity for the ring opening of epoxides catalyzed by chiral supported Cr(III)-salen complexes. Gigante, Barbara; Corma, A.; Garcia, Hermenegildo; Sabater, Maria J. Ineti, DTIQ Estrada do Paco do Lumiar, Lisbon, Port. Catal. Lett. (2000), 68(1,2), 113-119.
Indium metal and its halides in organic synthesis. Ranu, Brindaban C. Department of Organic Chemistry, Indian Association for the Cultivation of Science, Calcutta, India. Eur. J. Org. Chem. (2000), (13), 2347-2356.
Synthesis of C-glycosylic compounds using three-membered cyclic intermediates. Smoliakova, Irina P. Chemistry Department, University of North Dakota, Grand Forks, ND, USA. Curr. Org. Chem. (2000), 4(6), 589-608.

(Continued)

*Primary Examiner* — Johann Richter
*Assistant Examiner* — Kofi Adzamli
(74) *Attorney, Agent, or Firm* — Karen A. Harding

(57) ABSTRACT

The present invention relates to a process comprising the steps of reacting a substituted epoxide, and preferably a silicone containing substituted epoxide with at least one lithium acrylic acid salt, at least one acrylic acid and optionally at least one inhibitor at a temperature above about 60° C. to form a substituted hydroxy acrylate.

20 Claims, No Drawings

OTHER PUBLICATIONS

Lewis acid-catalyzed regiospecific opening of vinyl epoxides by alcohols. Prestat, Guillaume; Baylon, Christophe; Heck, Marie-Pierre; Mioskowski, Charles. CEA-CE Saclay, Service des Molecules Marquees, Departement de Biologie Cellulaire et Moleculaire, Gif sur Yvette, Fr. Tetrahedron Lett. (2000), 41(20), 3829-3831.

A platinum complex-catalyzed reaction of 3-chloro-1,3-diene monoepoxides with carbon nucleophiles involving nucleophilic substitution at the central carbon atom of the p-allyl ligand in the intermediate complex. Dependency of regioselectivity upon the added lewis acids. Kadota, Joji; Chatani, Naoto; Murai, Shinji. Department of Applied Chemistry, Faculty of Engineering, Osaka University, Suita, Japan. Tetrahedron (2000), 56(15), 2231-2237.

Dramatic rate acceleration in titanocene catalyzed epoxide openings: cofactors and Lewis acid co-catalysis. Gansauer, Andreas; Bluhm, Harald. Institut fur Organische Chemie der, Georg-August-Universitat, Gottingen, Germany. Chem. Commun. (Cambridge) (1998), (19), 2143-2144.

Lewis acid-mediated ring opening of propargylic epoxides: a stereospecific synthesis of 1,2-disubstituted homopropargylic alcohols. Bernard, Nicolas; Chemla, Fabrice; Normant, Jean F. Laboratoire Chimie Organo-Elements, CNRS, Universite Pierre Marie Curie, Paris, Fr. Tetrahedron Lett. (1998), 39(37), 6715-6718.

Ionic complex of VO2+ as a catalytic for the alcoholysis of epoxides and unsaturated ketones. Nikitin, Alexander V.; Kholuiskaya, Svetlana N.; Rubailo, Valentin L. Institute of Chemical Physics, Russian Academy of Science, Moscow, Russia. J. Chem. Biochem. Kinet. (1997), 3(1), 37-44.

Stereoselective synthesis of five and/or six membered ring hydroxylactones obtained by Lewis acid mediated reaction of g,d-epoxy-b-hydroxyesters; access to 5-methylated 2-deoxy sugars. Nacro, Kassoum; Baltas, Michel; Escudier, Jean-Marc; Gorrichon, Liliane. Synthese Physiochemie Organique, Univ. Paul Sabatier, Toulouse, Fr. Tetrahedron (1997), 53(2), 659-672.

On the mechanism of alcoholysis of allylic and benzylic alcohols and of epoxides in the presence of ceric ammonium nitrate. Chapuzet, Jean-Marc; Beauchemin, Sophie; Daoust, Benoit; Lessard, Jean. Centre Recherche Electrochimie Electrocatalyse, Univ. Sherbrooke, Sherbrook, PQ, Can. Tetrahedron (1996), 52(12), 4175-80.

High-Speed "Immortal" Polymerization of Epoxides Initiated with Aluminum Porphyrin. Acceleration of Propagation and Chain-Transfer Reactions by a Lewis Acid. Akatsuka, Masaki; Aida, Takuzo; Inoue, Shohei, Faculty of Engineering, University of Tokyo, Tokyo, Japan. Macromolecules (1994), 27(10), 2820-5.

Remarkable selectivity in Lewis-acid-induced ring opening of 5-acetyl-10,11-dihydro-10,11-epoxy-5H-dibenz[b,f]azepine. Haasz, Ferenc; Galamb, Vilmos. Alkaloida Chem. Co. Ltd., Tiszavasvari, Hung. J. Chem. Res., Synop. (1993), (12), 494-5.

Meso-epoxides in asymmetric synthesis: enantioselective ring opening by nucleophiles in the presence of chiral Lewis acids. Paterson, Ian; Berrisford, David J. Angew. Chem., Int. Ed. Engl., 1992, 31(9), 1179-80.

Zeolite catalyzed ring opening of epoxides to acetylated diols with acetic anhydride. Ramesh, P.; Reddy, V. L. Niranjan; Venugopal, D.; Subrahmanyam, M.; Venkateswarlu, Y. Organic Chemistry Division-I, Indian Institution of Chemical Technology, Hyderabad, India. Synth. Commun. (2001), 31(17), 2599-2604.

Highly regioselective ring opening of epoxides and aziridines using cerium(III) chloride. Sabitha, G.; Satheesh Babu, R.; Rajkumar, M.; Reddy, C. S.; Yadav, J. S. Organic Division I, Indian Institute of Chemical Technology, Hyderabad, India. Tetrahedron Lett. (2001), 42(23), 3955-3958. CODEN: TELEAY ISSN: 0040-4039. Journal written in English.

Synthesis of multifunctionalized phosphonic acid esters via opening of oxiranes and azetidinium salts with phosphoryl-substituted carbanions. Bakalarz-Jeziorna, Agata; Helinski, Jan; Krawiecka, Boxena. Centre of Molecular and Macromolecular Studies, Polish Academy of Sciences, Lodz, Pol. J. Chem. Soc., Perkin Trans. 1 (2001), (9), 1086-1090.

Bis-chlorodibutyltin oxide as a new reagent for a mild, versatile and regioselective ring-opening of epoxides. Salomon, Claudio J. Departamento Farmacia, IQUIOS (CONICET), Facultad de Ciencias Bioquimicas y Farmaceuticas, Universidad Nacional de Rosario, Rosario, Argent. Synlett (2001), (1), 65-68.

Synthesis of Functionalized g-Spirolactone and 2-Oxabicyclo[3.3.0]octane Derivatives from Nucleophilic Oxirane Ring Opening. De los Santos, M. R.; Barreiro, E. J.; Braz-Filho, R.; Fraga, C. A. M. Departamento de Quimica, PPGQO, Universidade Federal Rural do Rio de Janeiro, Seropedica, Brazil. Tetrahedron (2000), 56(30), 5289-5295.

Fluorinated epoxides 5. Highly selective synthesis of diepoxides from a,w-diiodoperfluoroalkanes. Regioselectivity of nucleophilic epoxide-ring opening and new amphiphilic compounds and monomers. Cirkva, V.; Gaboyard, M.; Paleta, O. Technicka 5, Department of Organic Chemistry, Prague Institute of Chemical Technology, Prague, Czech Rep. Journal of Fluorine Chemistry (2000), 102(1-2), 349-361.

Iron(III) trifluoroacetate as an efficient catalyst for solvolytic and nonsolvolytic nucleophilic ring opening of epoxides. Iranpoor, Nasser; Adibi, Hadi. Chem. Dep., Shiraz University, Shiraz, Iran. Bull. Chem. Soc. Jpn. (2000), 73(3), 675-680.

Selective ring-opening of w-epoxyalkyl (meth)acrylates. An efficient access to bifunctional monomers. Olszewski-Ortar, Agnes; Gros, Philippe; Fort, Yves. Laboratoire de Chimie Organique 1, Faculte des Sciences, associe au CNRS, INCM, Universite H. Poincare—Nancy-I, Vandoeuvre-les-Nancy, Fr. Tetrahedron Lett. (1997), 38(50), 8699-8702.

Regiochemical control of the ring opening of 1,2-epoxides by means of chelating processes. 10. Synthesis and ring opening reactions of mono- and difunctionalized cis and trans aliphatic oxirane systems. Azzena, Francesca; Calvani, Federico; Crotti, Paolo; Gardelli, Cristina; Macchia, Granco; Pineschi, Mauro. Dip. Chim. Bioorg., Univ. Pisa, Pisa, Italy. Tetrahedron (1995), 51(38), 10601-26.

Regiochemical control of the ring opening of 1,2-epoxides by means of chelating processes. 6. Opening reactions of 3,4-epoxytetrahydropyran. Chini, Marco; Crotii, Paolo; Gardelli, Cristina; Macchia, Franco. Dip. Chim. Bioorg., Univ. Pisa, Pisa, Italy. Tetrahedron (1994), 50(4), 1261-74.

One-pot synthesis of a,b-dihydroxy sulfides via titanium-promoted oxirane ring opening. Lin, Guoqiang; Shi, Zhicai; Zeng, Chunming. Shanghai Inst. Org. Chem., Chin. Acad. Sci., Shanghai, Peop. Rep. China. Tetrahedron: Asymmetry (1993), 4(7), 1533-6.

Oxirane ring-opening with alcohol catalyzed by organotin phosphate condensates. Complete inversion at tertiary and benzylic centers. Otera, Junzo; Niibo, Yoshihisa; Nozaki, Hitosi. Dep. Appl. Chem., Okayama Univ. Sci., Okayama, Japan. Tetrahedron (1991), 47(36), 7625-34.

Regiochemical control of the ring opening of 1,2-epoxides by means of chelating processes. 4. Synthesis and reactions of the cis- and trans-oxides derived from 3-[(benzyloxy)methyl]cyclohexene. Chini, Marco; Crotti, Paolo; Flippin, Lee A.; Gardelli, Cristina; Macchia, Franco. Dip. Chim. Bioorg., Univ. Pisa, Pisa, Italy. J. Org. Chem. (1992), 57(6), 1713-18.

Compounds of (iso-PrO)3TiX as novel reagents for regioselective oxirane ring opening. Raifel'd, Yu. E; Nikitenko, A. A.; Arshava, B. M. Jt. Lab. Carbohydr. Nucleosides Synth., Moscow Inst. Fine Chem. Technol., Moscow, USSR. Tetrahedron: Asymmetry (1991), 2(11), 1083-4.

Ring-opening of oxiranes by silyl-substituted allyl anions. A regiochemical chameleon. Schaumann, Ernst; Kirschning, Andreas. Inst. Org. Chem., Univ. Hamburg, Hamburg, Fed. Rep. Ger. Tetrahedron Lett. (1988), 29(34), 4281-4.

Direct preparation of substituted olefins from epoxides utilizing lithium tetraalkylcerate. Ukaji, Yutaka; Fujisawa, Tamotsu. Chem. Dep. Resour., Mie Univ., Tsu, Japan. Tetrahedron Lett. (1988), 29(40), 5165-8.

* cited by examiner

PROCESS FOR THE PRODUCTION OF BIS(TRIMETHYLSILYLOXY)SILYLALKYL-GLYCEROL METHACRYLATES

RELATED PATENT APPLICATIONS

This patent application claims priority of a provisional application, U.S. Ser. No. 60/483,846, which was filed on Jun. 30, 2003.

FIELD OF THE INVENTION

The present invention relates to processes for the production of silicone monomers and particularly bis(trimethylsilyloxy)silylalkyl glycerol methacrylates.

BACKGROUND OF THE INVENTION

Various silicone containing monomers have found utility as starting materials in the production of medical devices, such as ophthalmic devices and particularly, soft contact lenses having improved permeability to oxygen. One class of suitable monomers includes tris and bis(trimethylsilyloxy) silylalkylglycerol methacrylates ("SiAGMA"). One process for making SiAGMA includes reacting the epoxide of the SiAGMA with methacrylic acid and either the sodium, potassium or lithium salt of methacrylic acid and an inhibitor, such as hydroquinone monomethyl ether. Reaction conditions include heating for about 15 hours, and yields SiAGMA having a purity of between about 75 to 95% and a number of byproducts, including dimethacrylated byproducts. When included in the monomer mixes used to make ophthalmic devices such as contact lenses, the dimethacrylated byproducts can act as crosslinkers, which even in small quantities can change the modulus of the resulting device. Accordingly, the concentration of these difunctional byproducts must either be tightly controlled or minimized. Removal of the difunctional byproducts is conventionally done by a cumbersome silica gel column chromatography step.

Thus, there remains in the art for an improved process for the production of SiAGMA type compounds, and particularly one which minimizes the formation of difunctional byproducts.

SUMMARY OF THE INVENTION

The present invention relates to a process comprising the steps of reacting a substituted epoxide, and preferably a silicone containing substituted epoxide with at least one lithium acrylic acid salt, at least one acrylic acid and optionally at least one inhibitor at a temperature above about 60° C. to form a substituted hydroxy acrylate. Specifically, the present invention relates to a process comprising the step of reacting a first reaction mixture comprising substituted epoxide with at least one lithium salt, at least one acrylic acid at a temperature above about 60° C. for up to about one day to form a substituted hydroxy acrylate and said substituted epoxide

DESCRIPTION OF THE INVENTION

Suitable substituted epoxides include those of Formula I, below:

Wherein $R^1$ is any substituent which would not react with a nucleophilic compound.

Preferred epoxides include those shown in Formula II, below:

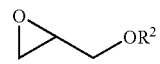

Wherein $R^2$ is a C1 to C12 alkyl substituted with at least one Si containing moiety and preferably at least one silicone. Suitable Si containing compounds include compounds of the formula III:

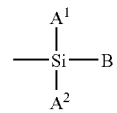

wherein $A^1$ and $A^2$ are the same or different and are selected from lower alkyl, alkyloxy and B;

B is lower alkyl, alkoxy or a group of the structure:

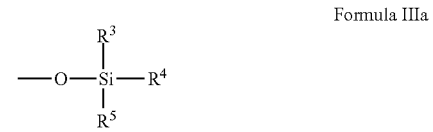

Formula IIIa

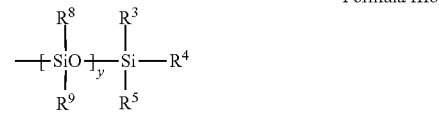

Formula IIIb wherein $R^3$, $R^4$, $R^5$, $R^8$ and $R^9$ are the same or different and are selected from the group including lower alkyl, phenyl, benzyl, and tri-alkyl siloxy substituents and y is an integer from 1 to 25. As used herein the term "lower alkyl" refers to alkyl groups comprised of 1 to 4 carbon atoms.

Specific examples of suitable epoxides include those of formula IV:

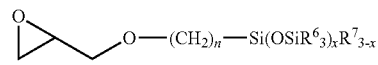

Wherein $R^6$ and $R^7$ are independently selected from alkyl groups having 1 to 4 carbon atoms, n is an integer between 1 and 12 and x is an integer between 0 and 3. Even more specifically, the epoxide may be the epoxide of (3-glycidoxypropyl)bis(trimethylsiloxy)methylsilane.

Epoxides may be formed in a number of ways including, but not limited to, oxidation of alkenes with peroxyacids, formation by an intramolecular $S_N2$ reaction of halohydrins, addition of a nucleophilic oxidizing agent (such as a basic solution of hydrogen peroxide) to an α,β-unsaturated carbonyl compound, and the reaction of a sulfonium ylide with a carbonyl compound. Alternatively, epoxides substituted with a Si containing group may be prepared by the hydrosilylation of an already formed epoxide containing an olefinic functionality. Such methods are well known to those skilled in the art and this list of synthetic routes to epoxides and epoxides substituted with a Si containing group, in no way limits the scope of this invention to these preparations.

According to the process of the present invention the epoxide is reacted with at least one acrylic acid and at least one lithium salt of said acrylic acid. Suitable acrylic acids comprise between 1 and 4 carbon atoms. Preferably said acid is methacrylic acid. The reaction between the epoxide and the acrylic acid may be equimolar, however, it may be advantageous to add an excess of acrylic acid. Accordingly, the acrylic acid may be used in amounts between about 1 and about 3 moles of acrylic acid per mole of the epoxide.

The lithium salts of the present invention comprise lithium and at least one acrylic acid comprising between 1 and 4 carbon atoms. Preferably said lithium salt is the Li salt of methacrylic acid. The lithium salt is added in an amount sufficient to catalyze the reaction, and preferably in an amount up to about 0.5 equivalents, based upon the epoxide.

An inhibitor may also be included with the reactants. Any inhibitor which is capable of reducing the rate of polymerization may be used. Suitable inhibitors include sulfides, thiols, quinines, phenothiazine, sulfur, phenol and phenol derivatives, mixtures thereof and the like. Specific examples include, but are not limited to hydroquinone monomethyl ether, butylated hydroxytoluene, mixtures thereof and the like. The inhibitor may be added in an amount up to about 10,000 ppm, and preferably in an amount between about 1 and about 1,000 ppm.

The reaction is conducted at elevated temperatures, preferably greater than about 60° C. and more preferably between about 80° C. and about 110° C. Suitable reaction times include up to about a day, preferably between about 4 and about 20 hours, and more preferably between six hours and about 20 hours. It will be appreciated by those of skill in the art the temperature and reaction time are inversely proportional, and that higher reaction temperatures may allow for decreased reaction times and vice versa. However, in the process of the present invention it is desirable to run the reaction to or near completion (for example, greater than about 95% conversion of substituted epoxide, and preferably greater than about 98% conversion of substituted epoxide).

It has been found that by using lithium as the metal ion in the salt, less impurities are generated at a given set of reaction conditions. Thus, the present invention provides a process for the production of substituted hydroxy acrylates in higher purities than by conventional methods. The substituted hydroxy acrylates may be further purified using super critical fluid extraction. Suitable extraction fluids are non-reactive with the silicone containing compounds to be purified and have critical points below the range which would cause degradation of the silicone containing compound. Examples include carbon dioxide, ethane, ethylene, propane, propylene, chlorotrifluoromethane, mixtures thereof, and the like. Carbon dioxide is a preferred supercritical fluid because it has a low critical point, is generally non-reactive with the silicone-containing compounds, non-flammable and environmentally benign.

Suitable conditions include one or more separation zones, where the supercritical fluid in the first zone comprises a density between about 0.5 and 0.7 g/ml and a density of 0.1 g/ml to about 0.3 g/ml. The desired densities may be achieved by controlling the pressure and temperature within the reaction zone. Any number of additional separation zones may be included.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

The following abbreviations are used in the examples below:

| | |
|---|---|
| SiMAA2 | bis(trimethylsilyloxy)methylsilylpropylglycerol methacrylate (CA Index name is 2-propenoic acid, 2-methyl, 2-hydroxy-3-[3-[1,3,3,3-tetramethyl-1-[(trimethylsilyl)oxy]disiloxanyl]propoxy]propyl) |
| MEHQ | hydroquinone monomethyl ether |
| Epoxide | (3-glycidoxypropyl)bis(trimethylsiloxy)methylsilane |

EXAMPLE 1

To a three-neck, 5000 mL round bottom reaction flask equipped with a magnetic stir bar, condenser with an attached drying tube, and a thermocouple, was added 92 g dry lithium methacrylate (1 mol, 0.17 equivalents) and 1023 grams methacrylic acid (11.91 mol, 2 equivalents). MEHQ (4.65 g, 0.037 mol, 0.006 equivalents) was added to the reaction flask. The reaction was stirred. With stirring, was added 2000 grams of Epoxide (obtained from Wright Corporation, 5.95 mol). The reaction mixture was heated to 90° C.

After about fifteen hours, the reaction mixture was removed from heat, allowed to cool to about 50° C. and transferred to a separatory funnel using ≈3200 mL hexanes (to give a 1:1 ratio of reaction mixture to hexanes) for transfer and to dilute the reaction mixture. The hexanes layer was washed successively with 4×≈3200 ML and 1×2000 mL 0.5 M aqueous NaOH, and 3×3200 mL 2.5 weight % aqueous NaCl. The organic layer was then dried over 250 gm $Na_2SO_4$ and filtered.

To the filtrate was added 800 g of flash grade silica gel. The heterogeneous mixture was agitated for three hours at room temperature and filtered over a fritted glass funnel. The filtrate was then concentrated on the rotary evaporator, at 55° C., to give SiMAA2. The resulting SiMAA2 was analyzed by LC-MS for purity. Purity results are listed in Table 1, below.

EXAMPLE 2

To a three-neck, 5000 mL round bottom reaction flask equipped with a magnetic stir bar, condenser with an attached drying tube, and a thermocouple, was added 59 g dry potassium methacrylate (0.476 mol, 0.08 equivalents) and 1023 grams methacrylic acid (11.91 mol, 2 equivalents). MEHQ (4.65 g, 0.037 mol, 0.006 equivalents) was added to the reaction flask. The reaction was stirred. With stirring, was added 2000 grams of Epoxide (obtained from Silar, 5.95 mol). The reaction mixture was heated to 100° C.

After about fifteen hours, the reaction mixture was removed from heat, allowed to cool to room temperature and transferred to a separatory funnel using ≈2000 mL hexanes for transfer and to dilute the mixture. The hexanes layer was washed successively with 3×≈5000 mL 0.5 M aqueous NaOH, and 3×≈3500 mL 2.5 weight % aqueous NaCl. The organic layer was then dried over $Na_2SO_4$ and filtered. The filtrate was then concentrated on the rotary evaporator, at 55° C., to give SiMAA2. The resulting SiMAA2 was analyzed by LC-MS for purity. Purity results are listed in Table 1, below.

TABLE 1

|  | Example 1 | Example 2 |
|---|---|---|
| Total Purity (%) | 85.9 | 84 |
| Difunctional impurities(%) | 4.92 | 8.97 |
| Ethyl Acetate(%) | <0.02 | 0.43 |
| Hexanes(%) | <0.06 | <0.6 |
| Epoxide(%) | 0.59 | <0.06 |
| Glycol(%) | 0.49 | 0.76 |

Difunctional impurities include the following compounds

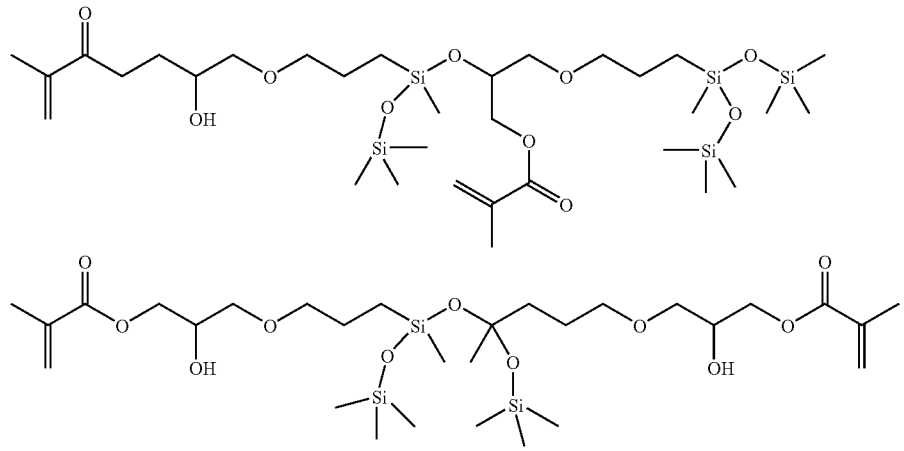

Glycol is

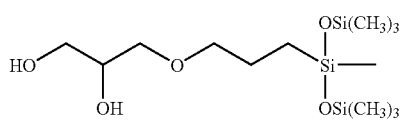

EXAMPLES 3-8

To a three-neck, 125 mL round bottom reaction flask equipped with a magnetic stir bar, condenser with an attached drying tube, and a thermocouple, was added 6.88 gm methacrylic acid and methacrylic acid salt listed in Table 2, in the amounts listed in Table 2. The reaction was stirred. With stirring, was added 13.44 g Epoxide (obtained from Silar, 40 mmol). The reaction mixture was heated to 90° C.

After fourteen hours, the reaction mixture was removed from heat, allowed to cool to about 50° C. and transferred to a separatory funnel using ≈21.5 mL hexanes for transfer and to dilute the mixture. The hexanes layer was washed successively with 3×≈33.3 mL 0.5 N aqueous NaOH, and 3×≈33.3 mL 2.5 weight % aqueous NaCl. The organic layer was then dried over $Na_2SO_4$ and filtered. The resulting SiMAA2 was analyzed by LC-MS for purity. Purity results are listed in Table 2, below.

TABLE 2

| Ex # | Salt | MAA salt (g) | Toluene (mL) | Purity |
|---|---|---|---|---|
| 3 | Li | 0.575 | — | 87.8 |
| 4 | K | 0.776 | — | 82.8 |
| 5 | Na | 0.676 | — | 86.2 |
| 6 | Li | 1.8 | 10 | 89.9 |
| 7 | K | 2.425 | 10 | 38.8 |
| 8 | Na | 2.11 | 10 | 86.1 |

We claim:

1. A process comprising the step of reacting a first reaction mixture comprising substituted epoxide, a catalyst of at least one lithium salt comprising acrylic acid and methacrylic acid, wherein said lithium salt is present in said reaction mixture in an amount up to about 0.5 equivalents, based upon said epoxide, and at least one acrylic acid, at a temperature above about 60° C. for at least about 4 hours to form a substituted hydroxy acrylate.

2. The process of claim 1 wherein said substituted epoxide comprises at least one compound of Formula II

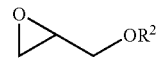

wherein $R^2$ is selected from the group consisting of C1 to C6 alkyls substituted with at least one Si containing moiety.

3. The process of claim 2 wherein $R^2$ is selected from the group consisting of C1 to C6 alkyls substituted with at least one siloxane.

4. The process of claim 1 wherein said substituted epoxide comprises at least one compound of formula III:

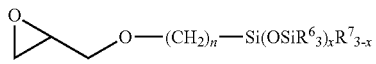

wherein $R^6$ and $R^7$ are independently selected from alkyl groups having 1 to 4 carbons, n is an integer between 1 and 12 and x is an integer between 0 and 3.

5. The process of claim 2 wherein said Si containing moiety has the formula:

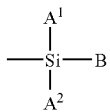

wherein $A^1$ and $A^2$ are the same or different and are selected from lower alkyl and B, B is a group of the structure:

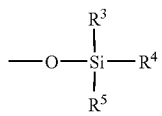

wherein $R^3$, $R^4$ and $R^5$ are the same or different and are selected from the group including lower alkyl, phenyl, benzyl, and tri-alkyl siloxy substituents.

6. The process of claim 1 wherein said substituted epoxide comprises (3-glycidoxypropyl)bis(trimethylsiloxy)methylsilane.

7. The process of claim 1 wherein said at least one lithium salt comprises between one and four carbon atoms and said at least one acrylic acid comprises between one and four carbon atoms.

8. The process of claim 1 wherein said acrylic acid comprises methacrylic acid.

9. The process of claim 1 wherein said acrylic acid is used in amounts between about 1 and about 3 moles of acrylic acid per mole substituted epoxide.

10. The process of claim 1 wherein said temperature is between about 80° C. and about 110° C.

11. The process of claim 1 wherein said reacting step is conducted until substantially all of said epoxide is converted to said substituted hydroxy acrylate.

12. The process of claim 1 wherein said at least one lithium salt is dry.

13. The process of claim 1 wherein said first reaction mixture further comprises at least one inhibitor.

14. The process of claim 13 wherein said inhibitor is selected from the group consisting of sulfide, thiol, quinone, phenothiazine, sulfur and mixtures thereof.

15. The process of claim 13 wherein said inhibitor is added in an amount up to about 10,000 ppm.

16. The process of claim 13 wherein said inhibitor is added in an amount between about 1 and about 1,000 ppm.

17. The process of claim 1 or 10 wherein said process is conducted for a reaction time between about 4 and about 20 hours.

18. The process of claim 13 wherein said inhibitor is selected from the group consisting of hydroquinone monomethyl ether, butylated hydroxytoluene and mixtures thereof.

19. The process of claim 1 further comprising the step of subjecting said substituted hydroxy acrylate to purification by supercritical fluid extraction.

20. The process of claim 19 wherein said supercritical fluid is carbon dioxide.

* * * * *